United States Patent [19]
Goddard

[11] 3,939,215
[45] Feb. 17, 1976

[54] CHEMICAL PROCESS
[75] Inventor: Lloyd E. Goddard, Orangeburg, S.C.
[73] Assignee: Ethyl Corporation, Richmond, Va.
[22] Filed: May 22, 1974
[21] Appl. No.: 472,352

[52] U.S. Cl....... 260/624 A; 260/621 A; 260/627 R
[51] Int. Cl.²................... C07C 39/06; C07C 37/22
[58] Field of Search............ 260/624 A, 624 R, 627, 260/621 A, 621 B, 627 R

[56] References Cited
UNITED STATES PATENTS

| | | | |
|---|---|---|---|
| 2,831,898 | 4/1958 | Eche et al............................ | 260/624 |
| 3,048,563 | 8/1962 | Seydel et al. .................... | 260/45.95 |
| 3,133,974 | 5/1964 | Curry et al........................... | 260/624 |

Primary Examiner—James O. Thomas, Jr.
Assistant Examiner—W. B. Lone
Attorney, Agent, or Firm—Donald L. Johnson; Robert A. Linn; Joseph D. Odenweller

[57] ABSTRACT

Aluminum is removed from sec-alkyl phenolic compositions containing aluminum in the form of a phenate by first adding aqueous alkali metal hydroxide in stoichiometric excess over said aluminum and then acidifying the mixture with a mineral acid and removing the acidic aqueous phase to leave a substantially aluminum-free sec-alkyl phenolic composition. The method is especially adapted to remove aluminum from the distillation bottoms remaining after distilling product from a sec-alkylation mixture formed by alkylating a phenol with a sec-alkyl precursor olefin using an aluminum phenate catalyst.

5 Claims, No Drawings

CHEMICAL PROCESS

BACKGROUND

Phenols are readily alkylated by reaction with olefins using an aluminum phenate catalyst (Ecke et al, U.S. Pat. No. 2,831,898). When this process is used to introduce sec-alkyl groups, higher temperatures are required compared to the introduction of tert-alkyl groups. Aluminum remaining in the reaction following the alkylation is particularly difficult to remove from such sec-alkylphenol compositions. For example, residual aluminum can be removed from tert-alkylphenol compositions by washing with aqueous acid under moderate conditions, but when this is applied to sec-alkylphenol compositions the aluminum is not removed without resorting to refluxing the sec-alkylphenol with the mineral acid.

SUMMARY OF THE INVENTION

According to the present invention, it has now been discovered that aluminum can be readily removed from sec-alkyl phenolic compositions formed by reacting a phenol with a sec-alkyl precursor olefin in the presence of an aluminum phenoxide catalyst by first adding aqueous alkali metal hydroxide to the composition and then acidifying the mixture with mineral acid. By this method almost complete extraction of the aluminum is accomplished under moderate temperature conditions.

DESCRIPTION OF THE PREFERRED EMBODIMENTS

A preferred embodiment of this invention is a method of removing aluminum from a sec-alkylphenol composition, said composition resulting from the alkylation of phenol with a sec-alkyl precursor olefin in the presence of an aluminum phenoxide catalyst, said composition containing aluminum, said method comprising (a) adding to said sec-alkylphenol composition an aqueous solution of an alkali metal hydroxide in an amount such that said alkali metal hydroxide is in stoichiometric excess of said aluminum to form a caustic mixture, (b) adding to said caustic mixture a mineral acid in an amount in stoichiometric excess of said alkali metal hydroxide to form an acidic mixture, and (c) removing the acidic aqueous phase leaving a substantially aluminum-free sec-alkylphenol composition.

The alkylation of phenols by olefins using an aluminum phenoxide catalyst to form sec-alkylphenol compositions is known, as shown in Ecke et al, U.S. Pat. No. 2,831,898, incorporated herein by reference. Thus, the present invention can be defined as an improvement in a process of alkylating a phenol with a sec-alkyl precursor olefin using an aluminum phenoxide catalyst to obtain a sec-alkylphenol composition, according to which improvement the aluminum content of the resultant sec-alkylphenol composition is substantially removed by adding an alkali metal hydroxide to the sec-alkylphenol in an amount in stoichiometric excess of the aluminum content and then adding mineral acid to the mixture in an amount sufficient to acidify the mixture.

The method of conducting the phenol alkylation to obtain a sec-alkylphenol composition is fully disclosed in Ecke et al, U.S. Pat. No. 2,831,898. The useful starting phenols are described therein. The olefins which are precursors of sec-alkylphenols are those that have at least one hydrogen atom bonded to each of the two carbon atoms forming the olefinic double bond. These are illustrated by the following structure:

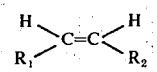

wherein $R_1$ is hydrogen or a hydrocarbon radical and $R_2$ is a hydrocarbon radical. The hydrocarbon radicals may be alkyl, cycloalkyl, aralkyl, aryl, and the like. Examples of such olefins include propylene, butene-1, 3-methyl butene-1, butene-2, 1-hexene, 1-dodecene, 1-tetradecene, 1-hexadecene, 1-eicosene, cyclohexene, cyclooctene, styrene, p-tert-butyl styrene, 3-phenylpropene-1, stilbene, 2,3-benzosytrene, and the like.

As described in U.S. Pat. No. 2,831,898, useful phenols include any hydroxy aromatic which has an unsubstituted position on a benzene ring ortho to a phenolic hydroxyl. These can be mono- or poly-nuclear and also mono- or poly-hydroxy phenols, as, for example, hydroxy benzenes, hydroxy anthracenes, hydroxy naphthalenes, hydroxy phenanthrenes, and the like. The phenol can also have other substituents on the aromatic ring, such as halogen or hydrocarbon substituents, for example, alkyl, alkaryl, aryl, and the like. Examples of phenols useful in the reaction include phenol, o-methylphenol, p-tert-butylphenol, o-ethylphenol, p-sec-butylphenol, α-naphthol, β-naphthol, 4,4-bisphenol, and the like, as disclosed by Ecke et al. Phenol itself is preferred.

The aluminum phenoxide is best made by adding aluminum metal granules or turnings to the phenol and heating to a temperature at which the aluminum reacts with the phenol to form aluminum phenoxide. This should be conducted under an inert atmosphere because hydrogen is evolved. With phenol and lower boiling phenolic reactants a closed system should be used to avoid loss of phenol. Reaction with aluminum will generally occur at about 150°–200°C.

A good reaction rate is obtained with the sec-alkyl precursor olefin when the amount of aluminum added to form phenoxide is sufficient to provide a phenol:aluminum mole ratio of about 30–100:1.

Sec-alkyl precursor olefin is added to the phenol reactant at a temperature of about 200°–300°C. A preferred temperature range is from about 220°–260°C.

The alkylation is carried out in a closed system and pressure depends on the vapor pressure of the phenol and olefin reactants at the reaction temperature. Generally, pressures of about 200 to 800 psig are observed.

It is generally desired to remove the aluminum from the reaction mixture either following the alkylation or after the o-sec-alkylphenol product has been distilled from the reaction mixture. Apparently because of the higher temperature employed in the alkylation to produce sec-alkylphenols compared to tert-alkylphenols, the aluminum is most difficult to remove. If it is not removed, the final residue after removal of the desired sec-alkylphenol product presents a difficult disposal problem. Such residues are usually disposed of by burning. If the aluminum is not substantially removed from the product an alumina ash is discharged into the atmosphere on burning. By subjecting the aluminum-containing sec-alkylphenol composition to the present process the alumina ash level is reduced generally to a level below 0.1 weight per cent. Thus, the present invention constitutes a method of decreasing air pollution upon burning distillation residues from an aluminum phenoxide catalyzed sec-alkylation process.

Another use for the sec-alkylphenol distillation bottoms is as a source for recovering phenol and olefin values by dealkylation of the residue. It is preferred to remove the aluminum content of the residue before subjecting it to a dealkylation process to avoid fouling of the dealkylation catalyst. Thus, the present process is useful for converting an aluminum-containing distillation residue to a valuable feed stock for a phenol dealkylation process.

The improvement of this invention is conducted by adding aqueous alkali metal hydroxide to the aluminum-containing reaction mixture either following the alkylation before distillation or following the distillation to remove product. Since the aluminum phenoxide catalyst generally does not interfere with the distillation of o-sec-alkyl phenolic products, it is preferred to defer the wash procedure until after the distillation since less volume will need to be processed.

The alkali metal hydroxide may be any that are reasonably available. The preferred materials are sodium hydroxide and potassium hydroxide.

The amount of alkali metal hydroxide should be at least stoichiometrically equivalent to the amount of aluminum in the phenolic composition. One mole of aluminum represents three equivalents and, hence, three moles of alkali metal hydroxide are stoichiometrically equivalent to one mole of aluminum. There is no real upper limit to the amount of alkali metal hydroxide used but, for practical considerations, an amount up to about 10 moles of alkali metal hydroxide per mole of aluminum is considered adequate.

The concentration of alkali metal hydroxide in the aqueous solution can vary over a wide range. For example, the concentration can vary from about 5 weight per cent up to a saturated solution. A preferred range is from about 25 weight per cent up to a saturated solution.

After adding the aqueous alkali metal hydroxide the mixture is stirred and warmed to accelerate the conversion of aluminum to an extractable form. Heating to about 30°-150°C, and preferably about 50°-100°C, for a period of about 5–60 minutes is generally adequate.

Following the caustic treatment, the mixture is acidified by adding a strong mineral acid such as HCl, $H_2SO_4$, $H_3PO_4$, and the like. Sulfuric acid is preferred. The amount added should be in stoichiometric excess of the amount of alkali metal hydroxide added such that the final mixture is acidic. It is preferably brought to a pH of 3.5 or lower, and more preferably a pH of about 3. The mixture is stirred for a period of about 5–60 minutes at about the same temperature as used in the alkali metal hydroxide treatment, and preferably below 100°C so that corrosion due to acid is minimized. Operation at a temperature of about 50°-100°C allows the use of stainless steel equipment whereas previous attempts to extract aluminum from sec-alkylphenol compositions which did not use a caustic pretreat required refluxing mineral acid and glass-lined equipment.

The method by which the improved aluminum extraction process is carried out is illustrated in the following example.

EXAMPLE 1

Phenol Alkylation with Butene-1

In a pressure reaction vessel place 940 grams of phenol and 5.4 grams of granular aluminum. Flush the vessel with nitrogen, seal and, while stirring, heat to 175°C and stir for 15 minutes. Cool to 50°C and vent evolved hydrogen. Pressurize with butene-1 to 400 psig and heat to 240°C. Maintain at 400 psig by continually feeding butene-1. Continue operation until 336 grams of butene-1 have been added (about 1 hour). Cool and vent. Transfer the reaction mixture to a distillation vessel and distill out unreacted phenol and o-sec-butylphenol as the desired product. The distillation is conducted such that o-sec-butylphenol distills at 127°–129°C at 30 mm Hg. Transfer the distillation residues to storage.

Aluminum Extraction

A 197.8 gram portion of accumulated distillation residue obtained as above was placed in a stirred reaction vessel. To this was added 20 ml of 50 weight per cent aqueous sodium hydroxide. This mixture was stirred at 80°C for 15 minutes and then 400 ml of 13 weight per cent aqueous $H_2SO_4$ was added over a 20 minute period. This was stirred 5 minutes and then the stirrer was turned off. The mixture rapidly separated into two sharp phases. The aqueous phase was removed, leaving an organic phase consisting mainly of di- and tri-sec-butylphenols having an ash content of 0.014 per cent.

EXAMPLE 2

In a stainless steel wash vessel was placed 538.5 grams of distillation residue as described in Example 1. While stirring, this was heated to 60°C and 87.8 grams of 50 per cent aqueous sodium hydroxide was added. Heat was applied to raise the temperature to 80°C and stirring continued for 30 minutes at this temperature. Then, 640 ml of water was added, followed by the slow addition of 300 grams of 40.7 weight per cent $H_2SO_4$. The pH of the mixture was 1.8. Stirring was continued 15 minutes at 80°C, at which time the stirrer was turned off and the mixture rapidly separated into two distinct phases. The lower aqueous phase was drained off and the remaining organic phase washed with dilute sodium carbonate to neutralize any remaining acid. This aqueous phase was drained off, leaving a low-ash phenolic composition consisting mainly of di- and tri-sec-butylphenols.

Application of the improved aluminum extraction procedure to other sec-alkylphenol compositions obtained from the aluminum phenoxide catalyzed alkylation of phenolic reactants with sec-alkyl precursor olefins will be apparent from the above in view of the fact that such alkylations are well known and only the fully-described aluminum extraction procedure is new. The procedure can readily be carried out by substituting an equivalent amount of other alkali metal hydroxides such as potassium hydroxide or other strong mineral acids such as hydrochloric or phosphoric.

The o-sec-butylphenol obtained according to the above examples is a useful product. It can be readily nitrated according to the method described in U.S. Pat. No. 2,810,767 to form 2,4-dinitro-6-sec-butylphenol, a selective herbicide.

I claim:

1. A method of removing aluminum from a sec-alkylphenol composition, said composition resulting from the alkylation of phenol with a sec-alkyl precursor olefin in the presence of an aluminum phenoxide catalyst, said composition containing aluminum, said method comprising (a) adding to said sec-alkylphenol composition an aqueous solution of an alkali metal hydroxide in an amount such that said alkali metal hydroxide is in stoichiometric excess of said aluminum to form a caustic mixture, (b) heating said caustic mixture at about 30°–150°C, (c) adding to said caustic mixture a mineral acid in an amount in stoichiometric excess of said alkali metal hydroxide to form an acidic mixture, (d) heating said acidic mixture at 30°–150°C and (e) removing the acidic aqueous phase leaving a substantially aluminum-free sec-alkylphenol composition.

2. A method of claim 1 wherein said sec-alkylphenol composition is a mixture of sec-butyl phenols.

3. A method of claim 2 wherein said mineral acid is sulfuric acid.

4. A method of claim 3 wherein said alkali metal hydroxide is sodium hydroxide.

5. A method of claim 4 wherein said sulfuric acid is added in sufficient stoichiometric excess over said sodium hydroxide such that the acidic mixture has a pH below 3.5.

* * * * *